United States Patent
Roettger et al.

(12)

(10) Patent No.: US 7,304,200 B2
(45) Date of Patent: Dec. 4, 2007

(54) METHOD FOR SEPARATION OF SUBSTANCES BY EXTRACTION OR BY WASHING THEM WITH IONIC LIQUIDS

(75) Inventors: Dirk Roettger, Recklinghausen (DE); Franz Nierlich, Marl (DE); Joerg Krissmann, Mainschaff (DE); Peter Wasserscheid, Cologne (DE); Wilhelm Keim, Aachen (DE)

(73) Assignee: OXENO Olefinchemie GmbH, Duesseldorf (DE)

( * ) Notice: Subject to any disclaimer, the term of this patent is extended or adjusted under 35 U.S.C. 154(b) by 505 days.

(21) Appl. No.: 10/503,550

(22) PCT Filed: Jan. 17, 2003

(86) PCT No.: PCT/EP03/00430

§ 371 (c)(1),
(2), (4) Date: Aug. 4, 2004

(87) PCT Pub. No.: WO03/070667

PCT Pub. Date: Aug. 28, 2003

(65) Prior Publication Data

US 2005/0090704 A1 Apr. 28, 2005

(30) Foreign Application Priority Data

Feb. 19, 2002 (DE) ................ 102 06 808

(51) Int. Cl.
*C07C 7/10* (2006.01)
*C07C 7/00* (2006.01)

(52) U.S. Cl. .................. 585/833; 585/809; 585/810; 585/860; 585/864

(58) Field of Classification Search ........... 585/809, 585/810, 833, 835, 860, 864
See application file for complete search history.

(56) References Cited

U.S. PATENT DOCUMENTS

| 6,339,182 B1* | 1/2002 | Munson et al. ............. 585/809 |
| 7,019,188 B2* | 3/2006 | Smith et al. ................ 585/809 |
| 2003/0125599 A1* | 7/2003 | Boudreau et al. ........... 585/809 |

FOREIGN PATENT DOCUMENTS

| WO | 0140150 | 6/2001 |
| WO | 0198239 | 12/2001 |
| WO | 0234863 | 5/2002 |

* cited by examiner

*Primary Examiner*—Glenn Caldarola
*Assistant Examiner*—Randy Boyer
(74) *Attorney, Agent, or Firm*—Oblon, Spivak, McClelland, Maier & Neustadt, P.C.

(57) ABSTRACT

The present invention relates to a process for the liquid-liquid extraction or liquid-gas extraction of mixtures of organic compounds, in which one or more components of the mixture are completely or partly extracted by means of a phase comprising at least one ionic liquid.

11 Claims, No Drawings

METHOD FOR SEPARATION OF SUBSTANCES BY EXTRACTION OR BY WASHING THEM WITH IONIC LIQUIDS

The present invention relates to a process for liquid-liquid or liquid-gas extraction, with a liquid phase comprising an ionic liquid being used for extraction.

Industrial separations of mixtures of substances are frequently carried out using distillations and rectifications. In these methods, components of the mixture are separated on the basis of their different boiling points or vapor pressures. If the components to be separated are not volatile, not stable in the gas phase or the vapor pressures of the components are too similar, a simple separation by distillation can no longer be carried out. Economic reasons also lead to alternatives to simple separation processes such as distillation or crystallization being sought.

One alternative is liquid-liquid extraction in which one or more of the components are concentrated in an extractant because of their better solubility and are thus separated off.

Liquid-liquid extractions are standard operations in process engineering. A comprehensive overview may be found, for example, in Ullmann's Encyclopedia of Industrial Chemistry, $5^{th}$ Edition, Wiley-VCH, Weinheim, Vol. B3, Chapter 6, "Liquid-Liquid Extraction".

The analogous concept, namely the preferential concentration (absorption) of one or more components to be separated in a second phase, can also be used for the separation of gas mixtures (hereinafter referred to as liquid-gas extraction). This is implemented industrially in the form of, for example, a gas scrub. These processes, too, are standard operations of process engineering and are described, for example, in Ullmann's Encyclopedia of Industrial Chemistry, $5^{th}$ Edition, Wiley-VCH, Weinheim, Vol. B3, Chapter 8, "Absorption".

Since the separation performance of these extraction processes is influenced considerably by the extractant used, many liquids have been examined for this purpose, including "ionic liquids".

The term "ionic liquids" has become established in the specialist literature as a name for salts which are liquid at room temperature. They have recently attracted increasing attention as "alternative" solvents, in particular their use as carrier phase for catalysts. An overview may be found in Angew. Chem. 2000, 112, 3926 to 3945.

Ionic liquids have also been discussed as extraction media for liquid-liquid extractions (Chem. Commun. 1989, p. 1765-1766). Here, the extraction of organic compounds such as phthalic acid or toluene from a 1-octanol/water mixture by means of a mixture of water and particular ionic liquids which have a miscibility gap with water has been examined and compared. It was found that charged or uncharged aryl compounds can be extracted from a lighter water phase into the heavier ionic liquid phase with a satisfactory sharpness of separation.

This publication discloses the use of ionic liquids in the extraction of water-soluble, e.g. polar or even ionic, organic compounds into a further very polar phase comprising ionic liquids. However, many separation problems in organic chemistry relate to nonpolar substances, preferably in the absence of an aqueous phase.

For example, the complete separation of C4-hydrocarbons purely by distillation is not economically feasible. This mixture is obtained, for example, in cracking processes. Apart from the target products ethene and propene, a C4 crack fraction comprising 1,3-butadiene, 1-butene, cis-2-butene, trans-2-butene, n-butane, isobutene and isobutane as main components is also obtained. Various concepts have been described in the specialist literature for the further processing of these compounds. This work-up usually starts with the butadiene being separated off or reacted selectively (for example by distillation in the presence of NMP or selective hydrogenation of the butadiene to n-butenes). Isobutene cannot be separated off from 1-butene by distillation in an industrially feasible manner and the separation is therefore generally carried out by selective etherification (for example with methanol to form methyl t-butyl ether). The separation of the 2-butenes from n-butane, in particular trans-2-butene from n-butane, by distillation has likewise not been achieved satisfactorily in industry.

EP 0 216 991 describes a separation of the 2-butenes from n-butane by extractive distillation using morpholine as solvent. This does make the separation possible, but requires a considerable input of heat energy (steam) which adversely affects the economic attractiveness.

It is an object of the present invention to examine the usability of ionic liquids in water-free liquid-liquid extractions or liquid-gas extractions. For the purposes of the present invention, the term "water-free" refers to mixtures of organic compounds in which the water concentration is less than 5000 ppm.

It has surprisingly been found that the extraction of uncharged organic compounds from a mixture of substances can be achieved by means of ionic liquids.

The present invention accordingly provides a process for the liquid-liquid extraction or liquid-gas extraction of mixtures of organic compounds, in which one or more components of the mixture are completely or partly extracted by means of a phase comprising at least one ionic liquid.

The process of the invention is used exclusively for the extraction of mixtures of organic compounds. This means that the ionic liquid used for the extraction and the mixture to be extracted have a miscibility gap. Further phases, e.g. an aqueous phase which is immiscible with the ionic liquid, are not used.

However, it is possible to use a mixture of water and an ionic liquid as extractant.

It is possible to use a plurality of ionic liquids in admixture with one another. However, use is generally made of one ionic liquid as extractant or part of an extractant.

In the extraction according to the invention, a liquid phase comprising at least one ionic liquid is brought into contact with at least one further liquid or gaseous phase. The phase in which the ionic liquid is present can consist entirely of this or further comprise additional components such as hydrocarbons (saturated and/or unsaturated), alcohols (diols, polyols), carboxylic acids, carboxylic esters, lactones, lactams (for example NMP), amides, nitriles (for example acetonitrile), carbonates and amines. If the ionic liquid is worked up after the extraction and wholly or partly reused in the extraction, residues of the components from the previous extraction may also be present. If the ionic liquid is miscible with water, a corresponding aqueous system is also conceivable.

The other phase, i.e. the phase to be extracted, comprises the substance to be extracted in dissolved form and no or virtually no water. Mixtures of organic compounds can be extracted by means of the process of the invention. Such mixtures are obtained, for example, when the substance to be extracted is liquid under the extraction conditions and is to be separated from another liquid. In the case of liquid-gas extractions, a mixture of gases is present in the gas phase.

If the ionic liquid is used in admixture with further components as extractant, the proportion by weight of the ionic liquid in the extractant phase should be at least 25% by weight, preferably 50-100% by weight, particularly preferably 80-100% by weight.

The extraction in the process of the invention is based on the different solubility of individual components in the phase comprising the ionic liquid, not on the selective exchange of anions or cations between the individual phases.

The process is suitable for the extraction of mixtures of organic compounds which have the same number of carbon atoms (e.g. a $C_4$ crack fraction) or even isomeric compounds (e.g. isobutene and n-butene), preferably hydrocarbons.

Possible applications of the liquid-liquid extraction process of the invention are, for example, the extraction of olefins from a mixture of olefins and aliphatics, the extraction of multiply unsaturated compounds such as butadiene or acetylene from a mixture of monoolefins, dienes and polyenes and aliphatics, the extraction of aromatic compounds from a mixture of aliphatic and aromatic compounds, the extraction of aldehydes from mixtures of various aldehydes or, for example, the extraction of alcohols from mixtures of various alcohols.

The process is preferably used when the mixtures comprise organic compounds having the same number of carbon atoms, for example for the extraction of butadiene (usually together with alkynes, 1, 2-butadiene and vinylacetylene) from mixtures of C4-hydrocarbons, the extraction of butenes from mixtures of butenes and butanes, the separation of isobutene from other C4-hydrocarbons, the separation of propene and propane, the separation of isoprene from mixtures of C5-hydrocarbons or the separation of 2-methylbutanal and 3-methylbutanal.

The actual extraction procedure is as described in the prior art.

Various industrial embodiments of liquid-liquid extractions are known in the specialist literature (for example columns, mixer-settler combinations, centrifugal extractors). Further examples are described in Ullmann's Encyclopedia of Industrial Chemistry, 5$^{th}$ Edition, Wiley-VCH, Weinheim, Vol. B3, Chapter 6, "Liquid-Liquid Extraction". Preference is given to using processes in which the phases are conveyed in countercurrent. Furthermore, preference is given to processes which are operated isothermally or in which a temperature gradient is established during the extraction only as a result of different feed temperatures of extractant and the mixture to be extracted; the process of the invention is thus not carried out under distillation conditions. The process of the invention is likewise not carried out under the conditions of an extractive rectification. Preference is also given to processes in which a temperature gradient due to the feed temperatures is no greater than 80° C., particularly preferably less than 40° C.

In one process variant, a liquid-liquid extraction is carried out. It is also possible in this case to use a gas or gas mixture which is gaseous under ambient conditions as long as at least one gas is present in liquid form under the extraction conditions. Thus, for example, propene and propane can be separated in a liquid-liquid extraction under superatmospheric pressure.

A further variant of the process of the invention is liquid-gas extraction. This is generally carried out like a gas scrub by means of a liquid, with countercurrent extraction being advantageous. In this case, preference is given to carrying out an extraction of a plurality of gases using a liquid phase which consists of at least one ionic liquid or comprises this in the abovementioned ratios. It is possible for at least one of these gases to be a liquid under ambient conditions (20° C., 756 torr) but a gas under extraction conditions. This process variant is suitable for the extractive separation of a mixture of liquids, with this mixture firstly being vaporized and this vapor (gas) being extracted by means of a liquid phase comprising an ionic liquid. The liquid-gas extraction of the invention can, for example, be carried out in countercurrent in trickle towers or columns having internals; in an appropriate temperature range, the use of a bubble column, i.e. the use of the liquid phase comprising an ionic liquid as continuous phase with a gas phase as disperse phase, is also conceivable.

In both cases, viz. liquid-liquid and liquid-gas extraction, the extraction can be carried out in countercurrent. Preference is given to processes in which the component to be extracted is removed completely, but at least to an extent of more than 50%, from the starting mixture.

The extractions are preferably carried out at pressures of from 0.1 to 64 bar, particularly preferably from 1 to 24 bar. The temperatures are in the range from −10° C. to 200° C., preferably from 20° C. to 120° C.

In liquid-liquid extractions, the mass ratio of the phases during the extraction is preferably from 1000:1 to 1:1000, particularly preferably from 100:1 to 1:100. In the case of liquid-gas extractions, the ratio of the volume throughputs of gas phase to liquid phase is preferably from 0.01 to 50 $m^3/m^3$ when the gas phase forms the disperse phase and preferably from 1 to 3000 $m^3/m^3$ when the liquid phase forms the disperse phase.

For the purposes of the present invention, ionic liquids are compounds which comprise at least one anion and at least one cation and are liquid at above 25° C.

Preference is given to ionic liquids in which a singly or multiply positively charged organic compound forms the cation. Examples of such cations are 1, 3-disubstituted imidazoles, N-substituted pyridines and quaternary ammonium or phosphonium ions.

In the process of the invention, particular preference is given to ionic liquids containing the following cations:

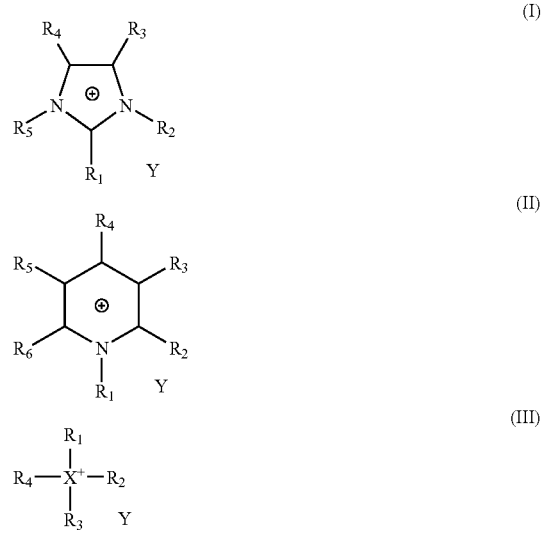

where
X=N, P
$R_1, R_2, R_3, R_4, R_5, R_6$=identical or different alkyl, alkoxy or aryl radicals each having 1-25 carbon atoms.

Typical anions of ionic liquids used according to the invention are halides, aluminates, borates, sulfates, sulfonates, anions of carboxylic acids and phosphates.

In the process of the invention, particular preference is given to ionic liquids containing the following anions Y:

$PF_6^-$, $Br^-$, $F^-$, $Cl^-$, $I^-$, $NO_3^-$, $AlCl_4^-$, $BF_4^-$, $B(R_7)_4^-$, $R_7OSO_3^-$, $R_7SO_3^-$, $R_7CO_2^-$, $R_7OPO_3^{2-}$ or $(R_7O)(R_8O)PO_2^-$, where $R_7$, $R_8$ are alkyl or aryl radicals each having 1-20 carbon atoms or H.

The ionic liquid used in the extraction is advantageously freed of the extracted components after the extraction and wholly or partly returned to the extraction. The extracted components can, for example, be separated off by distillation or by extraction. The components obtained by means of the extraction are often valuable raw materials for producing chemical products. Thus, butenes which are separated off from a mixture of butenes and butanes can be catalytically dimerized to $C_8$-olefins. These $C_8$-olefins can, for example, be converted by means of hydroformylation and hydrogenation into plasticizer alcohols which are used in plastics additives. 1,3-Butadiene, which is separated off from a mixture of $C_4$-hydrocarbons (cracker $C_4$) is a widely used basic chemical.

What is claimed is:

1. A process for liquid-liquid or liquid-gas extraction of olefins from a mixture of organic compounds including olefins and aliphatics, comprising:
   extracting the olefins using an ionic liquid phase;
   wherein the extraction is carried out in countercurrent; and
   the ionic liquid phase consists of:
   at least one ionic liquid; or
   the at least one ionic liquid and at least one additional component selected from the group consisting of hydrocarbons, alcohols, carboxylic acids, carboxylic esters, lactones, lactams, amides, nitriles, carbonates, amines and water.

2. The process as claimed in claim 1, wherein the organic compounds have the same number of carbon atoms.

3. The process as claimed in claim 1, wherein the organic compounds are isomers.

4. The process as claimed in claim 1, wherein the ionic liquid comprises compounds of the formula

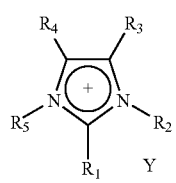

(I)

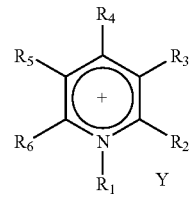

(II)

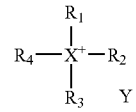

(III)

where

X=N, P $R_1$, $R_2$, $R_3$, $R_4$, $R_5$, $R_6$= identical or different alkyl, alkoxy or aryl radicals each having 1-25 carbon atoms, as cation.

5. The process as claimed in claim 1, wherein the ionic liquid comprises $PF_6^-$, $Br^-$, $F^-$, $Cl^-$, $I^-$, $NO_3^-$, $AlCl_4^-$, $BF_4^-$, $B(R_7)_4^-$, $R_7OSO_3^-$, $R_7SO_3^-$, $R_7CO_2^-$, $R_7OPO_3^{2-}$ or $(R_7O)(R_8O)PO_2^-$, where $R_7$, $R_8$ are alkyl or aryl radicals each having 1-20 carbon atoms or H, as anion Y.

6. The process as claimed in claim 1, wherein an extraction of a plurality of gases of which at least one is a liquid under ambient conditions but is present as a gas under the extraction conditions is carried out.

7. The process as claimed in claim 1, wherein an extraction of a plurality of liquids of which at least one is a gas under ambient conditions but is present as a liquid under the extraction conditions.

8. The process as claimed in claim 1, wherein butenes are extracted from a mixture of butenes and butanes.

9. The process as claimed in claim 1, wherein butadiene is extracted from a mixture of butenes and butanes.

10. The process as claimed in claim 1, wherein isobutene is extracted from a mixture of butenes and butanes.

11. The process as claimed in claim 1, wherein the proportion of ionic liquid in the extractant phase is at least 25% by weight.

* * * * *